United States Patent [19]
Guironnet

[11] Patent Number: 4,773,799
[45] Date of Patent: Sep. 27, 1988

[54] APPARATUS FOR SAMPLING A SECTION OF TUBE IN A NUCLEAR FUEL ASSEMBLY

[75] Inventor: Louis Guironnet, Lyon, France

[73] Assignees: Framatome, Courbevoie; Compagnie Generale Des Matieres Nucleaires, Velizy Villacoublay, both of France

[21] Appl. No.: 56,933

[22] Filed: Jun. 3, 1987

[30] Foreign Application Priority Data

Jun. 3, 1986 [FR] France .................. 86 07973

[51] Int. Cl.[4] .............. G21C 17/00; B23B 47/00
[52] U.S. Cl. .................... 408/150; 408/161; 82/4 C; 82/82; 30/358; 409/200; 376/261; 376/245; 29/723
[58] Field of Search .............. 376/261, 260, 245; 408/150, 151, 161, 162; 82/4 C, 82; 30/358, 361, 362, 263; 409/200; 29/723

[56] References Cited

U.S. PATENT DOCUMENTS

| 3,884,590 | 5/1975 | Skrentner et al. | 408/150 |
| 3,961,857 | 6/1976 | Koblesky | 408/150 |
| 4,142,429 | 3/1979 | Wilkens et al. | 82/4 C |
| 4,154,555 | 5/1979 | Skrentner | 408/150 |
| 4,522,780 | 6/1985 | Shallenberger et al. | 376/260 |
| 4,589,309 | 5/1986 | Nokovich | 82/82 |
| 4,667,547 | 5/1987 | Shallenberger et al. | 376/261 |
| 4,724,636 | 2/1988 | Tolino | 376/260 |

Primary Examiner—Deborah L. Kyle
Assistant Examiner—Daniel Wasil
Attorney, Agent, or Firm—Pollock, Vande Sande & Priddy

[57] ABSTRACT

For sampling a section of a tube in a nuclear fuel assembly comprising a skeleton formed by two end-pieces joined by tubes fixed to the end-pieces an opening for the extraction of the section through the upper end-piece is cut out with a milling cutter. Through the inside and by means of a cutting tool, the spacer tube is cut off at a level beneath the junction with the upper end-piece by means of a rotary tool introduced through the upper end-piece and the latter is extracted through the opening.

3 Claims, 3 Drawing Sheets

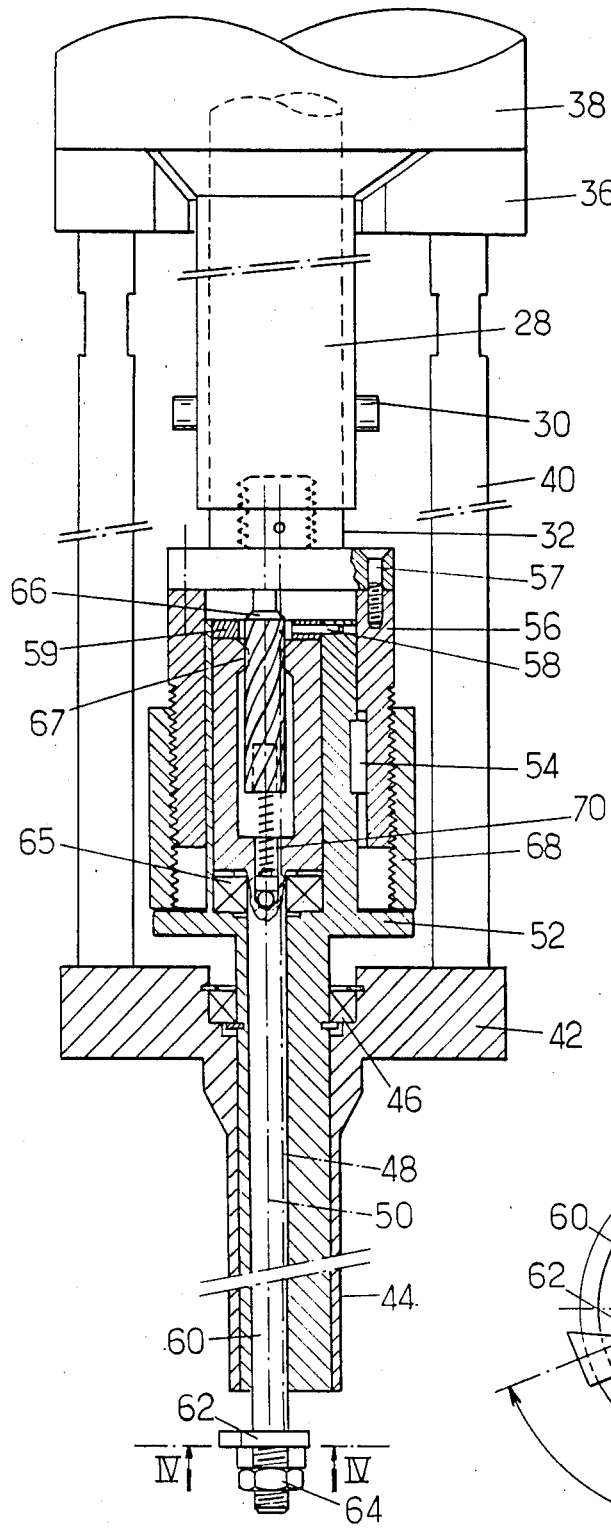
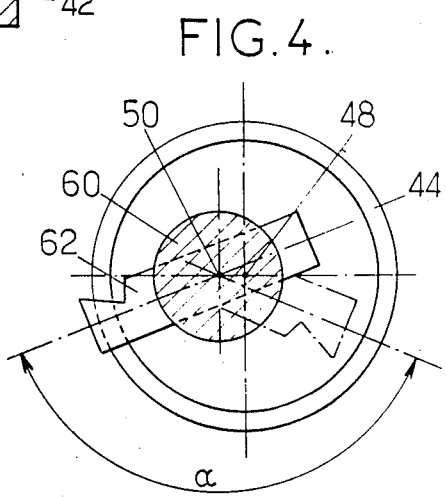
FIG. 3.
FIG. 4.

APPARATUS FOR SAMPLING A SECTION OF TUBE IN A NUCLEAR FUEL ASSEMBLY

BACKGROUND OF THE INVENTION

1. Field of the Art

The invention relates to an apparatus for sampling a section of tube in a nuclear fuel assembly of the type comprising a skeleton having two end-pieces and a plurality of grids distributed between the end-pieces along the tubes and arranged to retain a bundle of fuel elements between the end-pieces.

2. Prior Art

Most fuel assemblies of the above type used at the present time comprise tubes which constitute guides for rods of a control cluster. Each tube is fixed to the lower end-piece by a screw and to the upper end-piece by a sleeve crimped in the end-piece and projecting through the upper grid. It is often desirable to sample a section of the connecting structure between the tube and the upper end-piece to perform a corrosion examination on the sample providing an indication on the condition of the assembly skeleton.

At the present time, sampling is carried out generally upon complete dismantling of the assembly. To separate the upper end-piece from the tubes, a cutting tool is used which may be of various types inserted within the tube for sectioning it from inside. The tool may be as described in French No. 2,416,760. Processes and apparatus for completely dismantling fuel assembllies are also known (French No. 2,499,296).

SUMMARY OF THE INVENTION

It is an object of the invention to provide a method and an installation for sampling a section of tube in its connecting zone with the upper end-piece, whilst preserving the integrity of the assembly and without damaging fuel elements adjacent to the section sampled.

For that purpose, there is provided a method including the steps of: cutting out an opening for extraction of the section through the upper end-piece with a milling cutter; sectioning the tube from the inside under the junction thereof with the upper end-piece with a rotary tool inserted through the upper end-piece; and extracting a sample of the latter through the opening.

The method is particularly applicable to fuel assemblies whose tubes are fixed to a sleeve welded to the upper end-piece. Then it is possible to cut the assembly consisting of the tube and its fastening sleeve between the upper end-piece and the highest grid.

When the assembly must be handled after a tube section has been removed as a sample, it is of advantage to reinforce the connections between the remaining tubes and the upper end-piece before sampling. Reinforcement may be achieved by the method described in French Patent Application No. 86 05796.

There is also provided an apparatus for carrying out the above-defined method.

The invention will be better understood from the description which follows of a particular embodiment, given by way of example.

SHORT DESCRIPTION OF THE DRAWINGS

FIG. 3 shows a tool for cutting a section of tube and of sleeve for obtaining a sample;

FIG. 4 is a section along line IV—IV of FIG. 3.

DETAILED DESCRIPTION OF AN EMBODIMENT OF THE INVENTION

Figure 1:
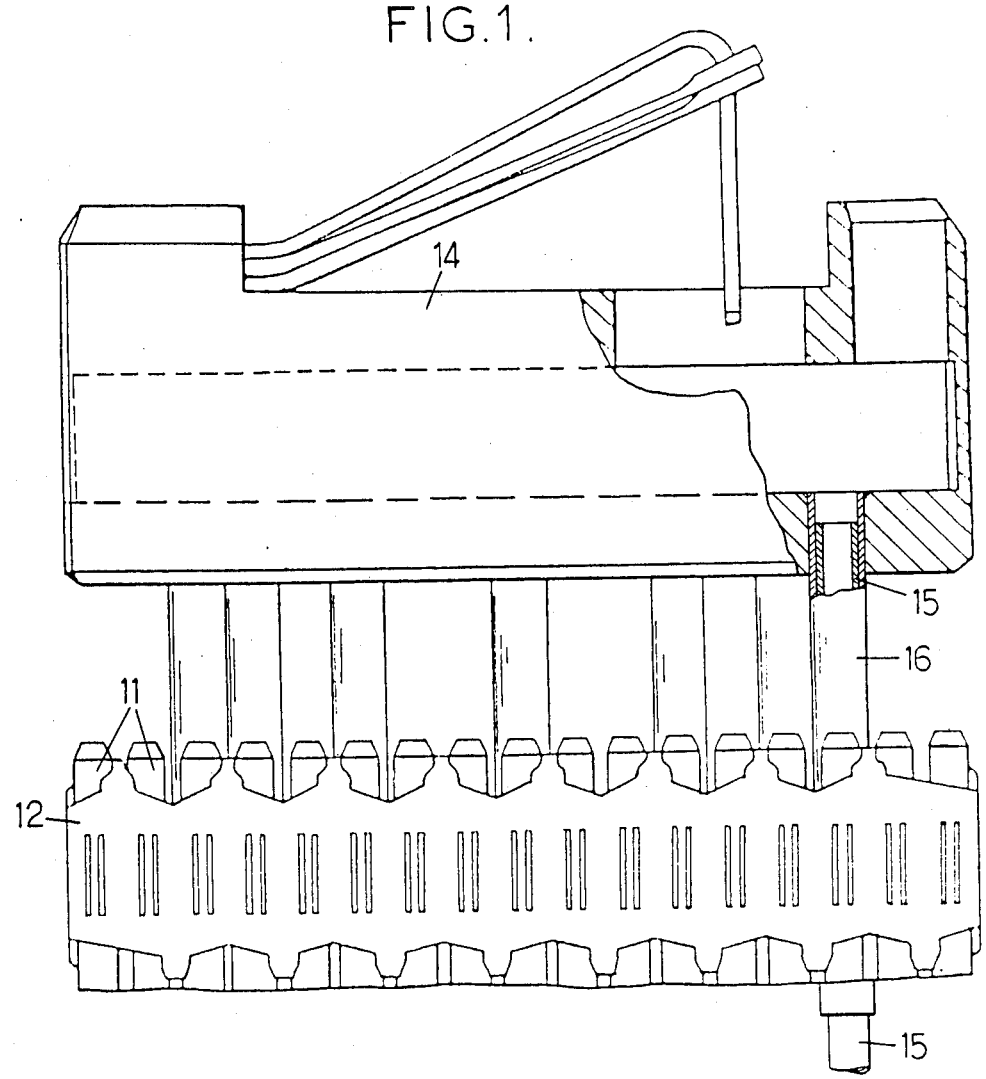
FIG. 1 is a diagrammatic view in elevation and in partial cross-section of the upper part of a fuel assembly to which the method according to the invention may be applied.
Figure 2:
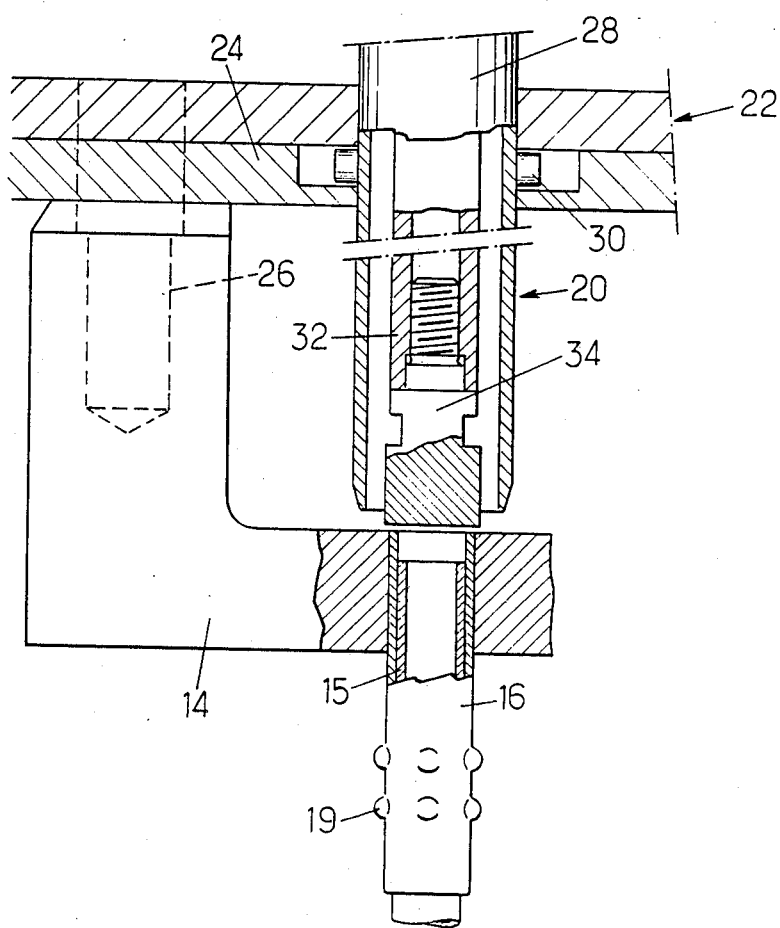
FIG. 2 shows diagrammatically, in elevation and in partial section, how an opening for extraction of a tube section is cut out in the adaptor plate of the upper end-piece shown in FIG. 1.

Referring to FIG. 1, a fuel assembly comprises a bundle of fuel elements 11 retained by grids 12 distributed along the bundle. The grids 12 define passages the majority of which are traversed by fuel elements 11. The other passages receive tubes 15. Each tube 15 is fixed to the lower end-piece (not shown) by connecting means, generally constituted by a screw to be dismountable. Each tube 15 is fixed to the upper end-piece 14 through a sleeve 16. As shown in FIG. 1, sleeve 16 is welded to the adaptor part of the end-piece 14. However, other connections are possible, for instance by radial expansion into a counterbore of the adaptor parts. The sleeve passes through the upper grid 12, to which it may be fixed, and terminates immediately under the grid. The tube 15 is fixed to the sleeve 16 by crimpings 19 at intermediate locations. As shown in FIG. 2, crimping is in the form of a plurality of local expansions. Additionally, the upper end of tube 15 may be crimped in the sleeve.

The tubes 15 are typically of zirconium-based alloy, whilst the sleeves are typically of stainless steel.

Cutting off and removal of a longitudinal section of the assembly of a tube 15 and its connection to the upper end-piece 14 involve, first, cutting out a passage opening in the upper end-piece 14, second, sectioning the assembly constituted by the tube 15 and the sleeve 16 for separating it from the balance of the tube.

Cutting out of an opening for passage of a tool

The opening may be cut out with a cutting tool similar to that described in European No. 138,711 to which reference may be made. FIG. 2 shows the lower part of the cutting tool 20, mounted on a mask 22 which guides the tool. The mask comprises a base plate 24 provided with pins 26 insertable in indexing and centering blind holes formed in the end-piece 14. The tool 20 comprises a sleeve 28 provided with retainer pins 30 for locking it in the base plate 24 of the mask 22 and a unit rotatably mounted in the sleeve 28 and connected to the shaft of a motor (not shown). The lower element of the rotary unit consists of a tubular spindle 32 internally threaded for receiving a bladed milling cutter 34, such as a hand wheel, or provided for moving the rotary mechanism downwards and upwards with respect to the sleeve 28. The milling tool may be formed with a suction passage (not shown) for drawing the chips and dust which collect in the annular space between the sleeve 28 and the spindle 32.

The opening for passage of the section to be extracted is cut out conventionally: the spindle 32 carrying the cutter 34 is rotated and progressively lowered until it has passed fully through the plate of end part 14. The outer diameter of the cutter must be large enough to permit removal of the section. If the connection between the tube and sleeve include projecting zones, as illustrated in FIG. 2, the opening formed by the cutter must have a sufficient diameter to permit these zones to pass.

Cutting off the tube and the sleeve

The tube 15 and sleeve 16 may be cut off with the milling tool of FIG. 2, after the cutter 34 has been replaced with an assembly as shown in FIGS. 3 and 4.

This assembly comprises a fixed structure comprising a fastening ring 36 which is connected, for example by screws (not shown), to the nose 38 of the stationary part of the tool. The structure also comprises tie rods 40, for example four in number, which connect the ring 36 to a supporting sole plate 42. The sole 42 has a downwardly extending tubular projection which constitutes a guide tube 44 and carries a ball bearing 46 coaxial with the spindle for receiving the rotary unit of the tool.

The rotary unit of the tool comprises a casing 52 rotating freely in the bearing 46 and having a key 54 engaging into an axial groove of a drive tube 56 for mutual sliding connection. An upper end piece is securely connected to tube 56, for instance by screws and has a threaded portion for connection with the spindle 32 in substitution for the cutter 34 of FIG. 2.

An upper end portion of casing 52 is tubular and defines a chamber receiving a bulged portion of a shank or shaft 60. A bearing 65 carried by the sleeve 52 supports the shank for mutual rotation about an axis 50 radially offset with respect to the axis 48 of the spindle 32, for a purpose which will be apparent below. An end shoulder of the bulged portion is maintained in abutting contact with the bearing 65 by a ring 59 fixed to casing 52 by a radial pin 58. The lower end portion of shank 60 projects out of the casing 52 and a cutter element 62 is secured thereto by a nut 64.

The rotary unit of the tool further comprises an adjustment shaft 65 whose axial displacement controls the angular portion of the cutter element 62 and consequently its amount of radial projection with respect to axis 48, since it rotates about the offset axis 50. For that purpose, a helical connection is provided between shaft 66 and shank 60. As shown in FIG. 3, it comprises helical grooves formed in shaft 66 and splines or fingers 67 of the bulged portion protruding into the grooves.

The distance from the end fitting at which the spacer tube 15 and the sleeve 16 will be cut off is determined by the length of the spindle 60 from the support represented by the sole 42. The sole is supported by a respective mask (not shown) which may be similar to those described in the above-mentioned patents.

The sequence of operations for cutting a sample is as follows. The nose of the tool is located on the fastening ring 36 of the stationary structure and the upper end piece of the drive tube 56 is fixed to spindle 32, while the spindle is in its uppermost portion. In that position, shaft 66 retains the cutter element 62 in retracted condition, as shown in dash-dot lines in FIG. 4. A return spring 70 may be provided for biasing the shaft and spindle upwardly. Then the motor of the tool is energized for driving the rotary unit and the rotary spindle of the tool is progressively lowered. Downward movement of the spindle 32 and shaft 66 causes the shank 60 to rotate about its axis due to the helical coupling between shaft 66 and the shank 60. Rotation of the shank 60 moves the cutting element 62 towards the position in which it is shown in solid lines in FIG. 4.

If the rotary unit of the cutting tool is maintained in rotation while a downward pressure force is maintained on spindle 66, the spacer tube 15, and then the sleeve 16 are progressively cut off.

Referring to FIG. 4, the amount of angular travel α, and hence the maximum radial projection of the cutter element 62, may be adjusted with an abutment ring 68 threadedly received on drive tube 56. Downward movement of the unit consisting of spindle 32, shaft 66, drive tube 56 and ring 68 is limited by abutment of ring 68 onto a radial flange of casing 52, as shown in FIG. 3. Preliminary adjustment of the final position of the cutting element eliminates the risk of damaging an adjacent fuel element.

During the cutting step, tube 15 and sleeve 16 are retained against rotation by the usual fastening of the sleeve 16 to the upper grid 12 and possibly the connections of tube 15 with other grids and the lower end-piece (not shown).

The cut-off section can then be removed, possibly along with the tool since it is supported by the cutter element 62 held in its position of maximum projection, and then introduced into a closable handling and protection container. Then the container may be transported to a laboratory for analysis.

Once the sampling has been carried out, the fuel assembly can again be handled, for example for transfer to a deactivation pool or for containment in a container, with an apparatus which may be as described in European No. 138 711 already mentioned.

I claim:

1. Sampling apparatus for taking up a longitudinal section of a tube in a nuclear fuel assembly comprising a skeleton having two end-pieces, a plurality of tubes fixed to and connecting the end-pieces and grids distributed between the end-pieces along the tubes and comprising a bundle of fuel elements retained by the grids between the end-pieces, including a power tool having:
   frame means including a sleeve provided with means for releasable connection of said sleeve with an end-piece of a nuclear fuel assembly, in alignment with a tube of said fuel assembly;
   a spindle arranged in said sleeve for rotation about and movement along a longitudinal axis of said sleeve,
   a cutter having means for releasable driving connection to said spindle at a distal end of said spindle, of such size as to cut out an opening in said end-piece upon rotation of said spindle of sufficient cross-section for passage of a section of said tube; and
   a sampling unit having a stationary part provided with means for fixed connection to said frame, a drive tube mounted in said stationary part for rotation about said axis of the sleeve and provided with connection means for non-rotatable axially slidable connection with the spindle in substitution for the cutter, and a shank mounted in the tube for rotation about an axis offset with respect to said longitudinal axis, carrying a radially directed cutting element and whose angular position in the tube about said axis is adjustable,
   and an adjustment shaft in said tube and axially displaceable with said spindle, connected to said shank via means which convert axial movement of said shaft into rotation of said shank.

2. Sampling apparatus for taking up a longitudinal section of a tube in a nuclear fuel assembly comprising a skeleton having two end pieces, and a plurality of tubes fixed to and connecting the end-pieces,
   comprising a power tool having:
   stationary frame means including a sleeve and support means connectable to said sleeve and provided with a tubular guide for abutment with an upper end-piece of a nuclear fuel assembly and alignment of said sleeve and tubular guide with a tube of said fuel assembly;

a spindle arranged in said sleeve for rotation about a longitudinal axis of said sleeve by a motor and manually movable along said longitudinal axis of said sleeve;

a drive tube mounted in said tubular guide for rotation about said axis and connected against axial movement relative to said tubular guide;

connecting means for providing a non-rotatable axially free connection between the spindle and drive tube;

a shank mounted in said drive tube for rotation about an axis offset with respect to said longitudinal axis and carrying a radially directed cutter element;

an axially directed shaft fast with said spindle and projecting into said drive tube;

means interconnecting said shaft and shank for converting downward movement of said spindle and shaft into rotation of said shank about said offset axis in a direction increasing the amount of radial projection of said cutter element from said longitudinal axis; and abutment means for limiting downward movement of said shaft and spindle with respect to said drive tube.

3. Sampling apparatus according to claim 2, wherein said abutment means comprises a flange on said drive tube, and an abutment ring threadedly received on a tubular part which belongs to said connecting means and is fast with said spindle.

* * * * *